(12) United States Patent
Bernoski

(10) Patent No.: US 6,370,418 B1
(45) Date of Patent: Apr. 9, 2002

(54) DEVICE AND METHOD FOR MEASURING THE POSITION OF A BONE IMPLANT

(76) Inventor: Franciscus Pieter Bernoski, Jan Willem Frisohof 18, NL-2517, LA Den Haog (NL)

( * ) Notice: Subject to any disclaimer, the term of this patent is extended or adjusted under 35 U.S.C. 154(b) by 0 days.

(21) Appl. No.: 09/381,342

(22) PCT Filed: Mar. 18, 1998

(86) PCT No.: PCT/NL98/00159

§ 371 Date: Sep. 20, 1999

§ 102(e) Date: Sep. 20, 1999

(87) PCT Pub. No.: WO98/41152

PCT Pub. Date: Sep. 24, 1998

(30) Foreign Application Priority Data

Mar. 18, 1997 (NL) .............................................. 1005565

(51) Int. Cl.[7] ..................................................................
(52) U.S. Cl. ..................................................... 600/426
(58) Field of Search .............................. 600/407, 424, 600/426, 429, 431; 606/130, 86, 96, 97; 623/11.11, 16.11

(56) References Cited

U.S. PATENT DOCUMENTS

| 4,841,975 | A | * | 6/1989 | Woolson | ..................... 378/205 |
| 5,577,089 | A | | 11/1996 | Mazess | |
| 5,806,518 | A | * | 9/1998 | Mittelstadt | ................... 600/407 |
| 5,871,018 | A | * | 2/1999 | Delp et al. | ................... 128/898 |
| 6,002,859 | A | * | 12/1999 | DiGioia, III et al. | .......... 623/19 |
| 6,074,394 | A | * | 6/2000 | Krause | ......................... 606/86 |

FOREIGN PATENT DOCUMENTS

WO  WO 96/25086  8/1996

OTHER PUBLICATIONS

K. Søballe et al., "Migration of Hydoxyapatite Coated Femoral Prostheses", The Journal of Bone and Joint Surgery, vol. 75b, No. 5, Sep. 1993, London, GB, pp. 681–687.

* cited by examiner

Primary Examiner—Brian L. Casler
(74) Attorney, Agent, or Firm—Young & Thompson

(57) ABSTRACT

A device and method for measuring the position of an implant that is connected to at least one bone in a body. The bone has at least one bone marking, and the implant has at least one predetermined identifying mark. The device includes generators for generating radiation and for directing the radiation onto the at least one bone marking and the at least one predetermined identifying mark of the implant from various directions. The device also includes receivers for receiving a radiation image and an evaluation device for determining the position of the implant with respect to the bone on the basis of the radiation image received. The evaluation device is able to recognize the shape of the at least one bone and to locate at least one or more bone markings on the basis of one or more anatomically fixed points on the bone.

16 Claims, 2 Drawing Sheets

DEVICE AND METHOD FOR MEASURING THE POSITION OF A BONE IMPLANT

BACKGROUND OF THE INVENTION

The present invention relates to a method for measuring the position of an implant relative to at least one bone in a body, to which bone the implant is connected, which bone has at least one bone marking, and which implant has at least one predetermined identifying mark, according to the following steps:

A. generating radiation and directing said radiation onto said at least one bone marking and said at least one predetermined identifying mark;

B. receiving a radiation image of said at least one bone marking and said at least one predetermined identifying mark;

C. determining the position of the implant with respect to the bone on the basis of the radiation image received in step B.

A method of this kind is in frequent use in hospitals and is described, for example, in K. Søballe, "Migration of hydroxyapatite coated femoral prostheses", Journal of Bone and Joint Surgery, volume 75-B, No. 5, September 1993, pp. 681–687.

U.S. Pat. No. 5,778,089 discloses a method and equipment for measuring forms and orientations of bones in living beings. This patent gives an analysis of how e.g. the morphology of the vertebrae can be established based on bone density measurements by means of X-ray detection. Use is made of a computer which analyses data received and which uses the data to accurately define the shape and size of the vertebrae under investigation. Moreover, the computer is programmed to use the data to indicate the vertebral condition in medical terms.

As a further example, U.S. Pat. No. 5,577,089 describes measurements with respect to the human femur. Here, anatomically fixed points, like the proximal limit and the medial epicondyle, are detected but they are only used to measure the femur length. Moreover, based on bone density measurements, a femur axis and a femur neck axis are calculated, as well as a femur head centerpoint. The patent discloses that these latter three features may be used to provide "an indication of any possible shifting of the prosthetic joint with respect to the femur" in case an artificial hip joint is implanted. Thus, U.S. Pat. No. 5,577,089 discloses measuring shifting of a prosthetic joint relative to a bone supporting this joint, based on bone density measurements. However, the method proposed is very laborious since it needs the calculation of the intersection of two imaginary lines, and of an imaginary femur head centerpoint, for which many data elements of the femur and the prosthetic joint need be established.

WO-A-96/25086 is directed to providing a solution for the problem that prosthetic devices may be lost over time. To that end, this document discloses a method of evaluating bone density around a radiolucent composite prosthesis. Since the prosthetic device is transparent to x-rays the prosthesis is provided with three radio-opaque reference markers embedded in the prosthesis. By means of a suitable densitometer, the boundaries of the prosthesis and the surrounding bone are identified and stored for later use. A region of interest is defined which is the area of the bone adjacent to the prosthesis. In this region of interest, the density of the bone is measured over time in order to establish any degradation of the bone to which the prosthesis is fixed. From the measurement data, the loosening of the prosthesis from the bone can be established.

The locations of the three radio-opaque markers are also stored in order to compare measurements later in time with prior measurements. To this end, a stored template with three template reference markers is used which are fitted to measured reference markers. To be sure that later measurements can be compared with former measurements, also, in the case of a hip implant, also the location of the lesser trochanter is identified and stored. Thus, both the three markers and the lesser trochanter are used to ensure that subsequent scans of a patient will be properly aligned and may be used for direct comparison with earlier scans.

A method of a first embodiment is used, for example, for determining the position of a hip prosthesis with respect to the femur, to which the hip prosthesis is connected on one side. On the other side, the hip prosthesis is in contact with an acetabular prosthesis, which is attached in the pelvis.

Wear to the hip joint leads to a very painful limitation of the movements which a person is able to carry out. Since the 1970s, hip prostheses have been widely used in orthopaedics to replace a hip joint which has become worn. However, treatment of the arthrosis does not end with the fitting of a hip prosthesis, but rather in practice is the beginning of a long period of careful monitoring of the patient. The monitoring consists both of physical examinations and of the study of regular X-rays.

When the method was introduced, the minimum age of patients to be treated was approximately 70 years. However, nowadays hip prostheses of this kind are also fitted to people of an increasingly young age. Younger people have a higher activity level than older people, with the result that hospitals are confronted to an increasing extent with hip prostheses which become detached from the bone to which they are connected.

FIG. 1 diagrammatically shows an X-ray of a hip prosthesis 1, which at the top is in contact, by means of a spherical end 2, with an acetabular prosthesis 19 which is attached to the pelvis 9, and at the bottom is connected by means of a pin 3 to the femur 6.

Just below the hip joint, the femur 6 has two marked projections, the outer projection 8 being referred to as the trochanter major and the inner projection 7 as the trochanter minor. The surface of the trochanter major is rough, so as to increase the contact area for the attached gluteus and thigh muscles. The trochanter minor lies on the inside and points 30° towards the rear. Only one muscle is attached to the trochanter minor, and this muscle, when tightened, causes the hip joint to bend and the femur to rotate outwards. Both tubercles are situated at a fixed location. This means that the shape, the location with respect to the leg and the size are not affected by positioning a prosthesis 1 in the femur. The trochanter major, the trochanter minor, as well as the axis of the knee joint (not shown in FIG. 1), are situated at fixed anatomical positions which form orientation points for the correct positioning of the prosthesis 1.

If a hip prosthesis 1 becomes detached from the femur 6, the result is that the prosthesis 1 slowly sinks into the femur 6, causing damage to the femur 6. If such an event is only discovered at a late stage, considerable amounts of bone may already have been lost, and this first has to be replaced with donor bone in order to repair the anatomy to a sufficient extent for the same prosthesis 1 to be replaced.

The "moment" at which the mechanical detachment occurs is not precisely known. With standard current X-ray techniques, it is only possible to detect whether a prosthesis is attached or has become detached, or at least whether the prosthesis 1 has moved more than 5 mm. In medical circles, the assumption is that the increase in the speed of migration is the "moment" of detachment. The speed of migration is understood to mean the rate at which the prosthesis 1 moves with respect to the femur 6.

The above-mentioned article by Søballe describes a standard procedure which can be used to measure the current position of the prosthesis 1 with respect to the femur 6. This method is known as the X-ray stereophotogrammetry analysis (RSA).

This standard procedure can be used to measure the movement of the prosthesis 1 in the femur 6 to an accuracy of 0.1 mm. In order to be able to make use of this standard procedure, during the hip operation it is necessary to arrange various small tantalum balls, which usually have a diameter of 0.8 mm, at various locations in the bone before fitting the hip prosthesis 1. Moreover, the prosthesis 1 itself also has to be provided with at least one small tantalum ball, which serves as a reference location. The small tantalum balls arranged in the bone no longer move after the hip operation.

In the RSA procedure, two X-ray cameras 10, 11 are used to take at least two different X-rays from different directions. The X-radiation is directed in such a way that the small tantalum balls in the femur 6 and on the prosthesis 1 are visible. By making use of the two pictures, which are taken from different angles, and a known trigonometric measurement, the spatial position of the prosthesis 1 can be accurately determined with respect to the femur 6. By repeating such measurements over the course of time, the migration of the prosthesis 1 with respect to the femur 6 can be determined. Measuring the migration of an implant relative to a bone to which the implant is connected, especially during the first year after the implant has been implanted, appears to be a good indication for possible future mechanical loosening, as is also indicated by another document directed to the RSA method: L. Ryd, Roentgen Stereophotogrammatic Analysis of Prosthetic Fixation in the Hip and Knee Joint, Clinical Orthopaedics and Related Research, Number 276, March, 1992.

Although the above-mentioned RSA procedure is extremely accurate, it is also extremely laborious. Moreover, this known method can only be used on a select group of patients, since only a few teaching hospitals have the advanced equipment which is required.

SUMMARY OF THE INVENTION

It is therefore desirable to provide a method which can be used to determine the migration of an implant, which is connected to a bone, in a body with a high level of accuracy but without extra actions, such as the attachment of small tantalum balls, being required during the operation prior to the attachment of the implant.

To achieve this object, the method of the above-mentioned type provides for the at least one bone marking to comprise an anatomically fixed point on the bone.

As is evident from a.o. U.S. Pat. No. 5,577,089 modern shape recognition means are available with which locations of anatomically fixed points on bones can be established. According to the invention, the locations of one or more of such anatomically fixed points may be used to establish the relative displacement between bones and implants connected to the bones. The method according to the invention is straightforward and uses only a limited number of process steps. No calculation of imaginary lines and centers is required to achieve a very reliable result.

The method according to the invention is not only applicable to implants portions of which are inserted into bone portion but also to medical supporting structures connected to the outside of bones. Therefore, for the purpose of this invention, "implants" are defined to include such supporting structures. It is no longer necessary to use, for example, small tantalum balls, the position of which is established with the aid of X-rays, but rather it is sufficient to use means for establishing the position of the at least one anatomically fixed point with respect to the prosthesis. In this case, to establish the position of the prosthesis, use is made of the location of, e.g., two identifying marks which are connected to the prosthesis. These identifying marks may, for example, as in the prior art, comprise small objects which can be located with the aid of X-rays, for example small tantalum balls. However, since it is nowadays possible to detect accurately shapes of objects, it is also possible to select, preferably, two fixed points on the prosthesis itself to be identifying marks, the location of which is established with the aid of shape recognition means. In this case too, there are therefore three known locations, with the aid of which respective positions can be determined with the aid of trigonometry.

It is not necessary for the method to make use of, e.g., two objects or points, which are to be located, on the implant and at least one bone marking. For example, one can alternatively use two anatomically fixed points on the bone and one identifying mark on the implant.

In a first embodiment the method comprises the following steps:

A1. generating first radiation at a first position and directing the first radiation onto the at least one bone marking (7, 8; 13, 14) and the at least one predetermined identifying mark (4, 5) of the implant (1; 15, 15') from a first direction;

A2. generating second radiation at a second position and directing the second radiation onto the at least one bone marking (7, 8; 13, 14) and the at least one predetermined identifying mark (4, 5) of the implant (1; 15, 15') from a second direction;

and step B comprises the following step:

B1. receiving first and second radiation images, respectively, of said at least one bone marking and said at least one predetermined identifying mark, formed by said first and second radiation, respectively;

and step C comprises the following step:

C1. determining the position of the implant (1; 15, 15') with respect to the bone (6; 16) on the basis of said first and second radiation images received in step B1.

The implant may, for example, be a hip prosthesis, in which case the bone marking may be selected from the following two anatomically fixed points: the trochanter major and the trochanter minor.

However, the method also relates to knee prostheses, in which case the bone marking is selected from the following two anatomically fixed points: the medial epicondyle and the lateral epicondyle.

Furthermore, the method according to the present invention may extend to any other form of prosthesis which is positioned in a bone where the bone has clearly recognizable, anatomically fixed points. The method is advantageous above all (but not exclusively) in joint-replacement implants, since all joints have unique bone markings.

In order to carry out the method outlined above, the invention also relates to a device.

BRIEF DESCRIPTION OF THE DRAWINGS

The invention will be explained in more detail below with reference to several drawings, which are intended only to illustrate the invention and not to limit it. In the drawings.

DETAILED DESCRIPTION OF THE PREFERRED EMBODIMENT

Figure 1:
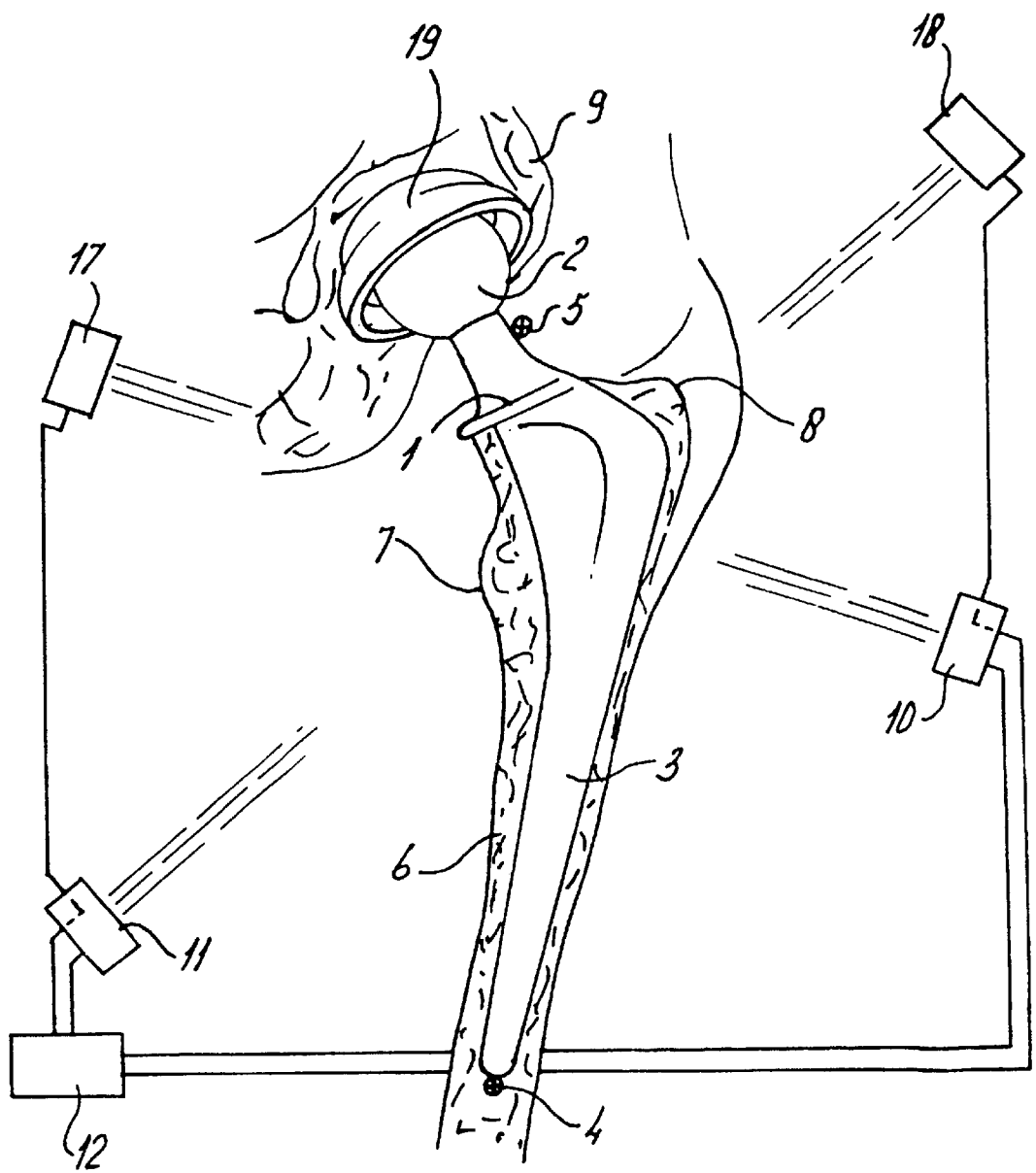
FIG. 1 shows a diagrammatic picture of a hip prosthesis which is connected to the femur.

The elements associated with the reference numerals 1 to 11 have already been described above. The reference numeral 12 indicates an evaluation device, for example a computer, which is connected to the radiation sources 10, 11. The radiation sources 10, 11 are designed to generate X-radiation. However, it is also conceivable that radiation of a different frequency may be generated and used for the purposes of the present invention. Theoretically, even ultrasound sources may be used.

The evaluation means 12 are designed, inter alia, to control the radiation sources 10, 11.

Furthermore, two receivers 17, 18 are provided for receiving the radiation emitted by the radiation sources 10, 11, after the radiation has radiated through the prosthesis with the surrounding bone. The receivers 17, 18 are connected to the evaluation device 12 for the purpose of transmitting the images which they receive.

The evaluation means 12 preferably comprise a computer, the memory of which has been loaded with a software program for recognizing shapes of bones. A program which can advantageously be used is the Scipio™ program, which has already been in use for some time in bone banks. Bone banks are establishments where bones are stored for subsequent use in transplants. The shape of bones stored in bone banks can be recognized with the aid of CCDs and the Scipio™ program. The shapes of the bones stored are recorded and held in a memory of a computer. In the event of requests for bones to be supplied, shapes of bones which have been requested can be compared with recorded shapes of bones, so that bones for transplant purposes can be supplied more easily and more quickly.

The above-mentioned Scipio™ program is in principle able to locate anatomically fixed points on bones.

The above-mentioned Scipio™ program can therefore in principle be used, for example, to locate the trochanter minor 7 and the trochanter major 8 of the femur. These points can then be used instead of the locations of the small tantalum balls which in the prior art are placed in the bone in order to determine the position of the femur 6.

To determine the position of the hip prosthesis 1, use can be made of the small tantalum balls 4, 5 which are connected to the prosthesis 1. However, there is no need to use these small tantalum balls. It will be clear that the Scipio™ program can recognize and record not only the shapes of bones, but also the shapes of implants. The Scipio™ program can therefore in principle also record and locate fixed points on implants. Hence it is then possible to carry out a trigonometric measurement which is known per se in order to establish the respective positions of the implant 1 and the bone 6.

It will be clear that the trigonometrical measurement only needs three points to be located. To do this, it is in principle unimportant whether two of the three points are connected to the bone 6 and one to the implant 1 or, as an alternative, one point is connected to the bone and two of the three points are connected to the implant 1. It is generally quite possible to locate two anatomically fixed points on the bone. As has been mentioned, the femur 6 has two anatomically fixed points, namely the trochanter minor 7 and the trochanter major 8.

Figure 2:
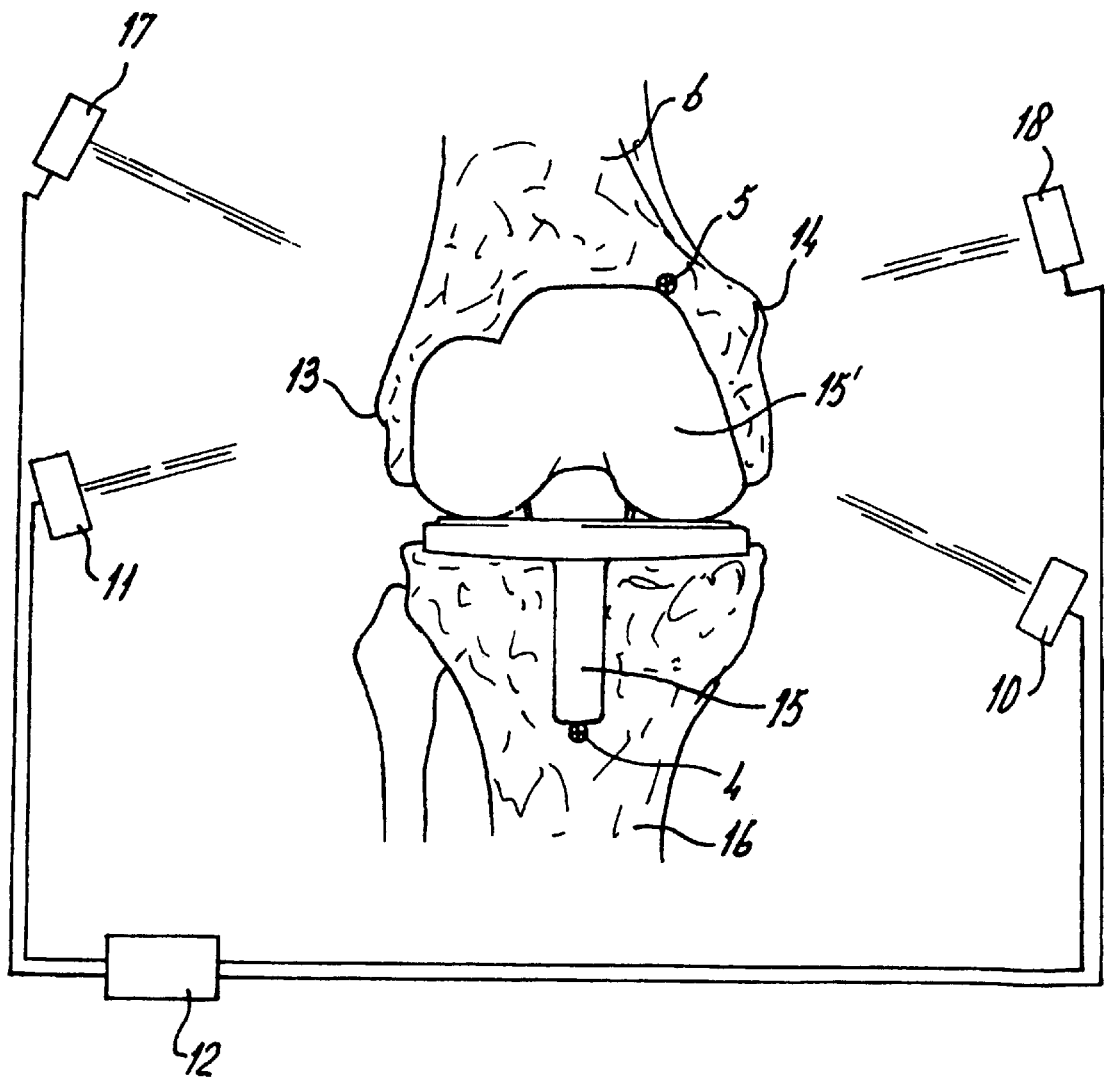
FIG. 2 diagrammatically shows a knee prosthesis which is connected to the femur and the tibia.

FIG. 2 diagrammatically shows a knee prosthesis 15, 15', which is connected to the femur 6 and the tibia 16.

In this case too, it is possible to make use of one or more anatomically fixed points, namely the medial epicondyle 13 and the lateral epicondyle 14.

Here too, it is the case that use may be made of small tantalum balls 4, 5 or that use may be made of a program which can record the shape of the knee prosthesis 15, 15' and then locate one or two fixed points thereon.

It will be clear that instead of trigonometrical measurements it is also in principle possible to use measurements which use more points.

The reference numerals 10, 11, 12, 17 and 18 in FIG. 2 refer to the same components as in FIG. 1.

Since the method and device described above no longer make use of separate small tantalum balls or the like placed in the bone, the abovementioned method can easily be employed in all hospitals where prostheses are fitted.

This means that the migration of a prosthesis with respect to the surrounding bone can be established in a simple and rapid manner.

It is extremely important that the migration of a prosthesis with respect to the surrounding bone is determined above all in the first few months after the prosthesis is fitted. This is because the extent of migration in the first few months has been found to be a measure of the probability of the prosthesis becoming detached. If it is found that the migration in the first few months is greater than a defined threshold, it can be decided to perform a surgical intervention, which can prevent needless disintegration of the bone. This means that interventions can be carried out more quickly, and there is less need to carry out revision operations in which damaged bone first has to be replaced before a new prosthesis can be fitted. This reduces the operation time and therefore saves considerable expense for the health service.

The receivers 17, 18 can be standard commercially available receivers which are provided with an image intensifier which is known per se. For this reason, there is no need for any more radiation for taking these X-rays, for example, than when taking conventional X-rays.

What is claimed is:

1. Method for measuring a position of an implant (1; 15, 15') relative to at least one bone (6; 16) in a body, to which bone the implant is connected, which bone (6; 16) has at least one bone marking (7, 8; 13; 14), and which implant has at least one predetermined identifying mark (4, 5), according to the following steps:

A. generating radiation and directing said radiation onto said at least one bone marking and said at least one predetermined identifying mark;

B. receiving a radiation image of said at least one bone marking and said at least one predetermined identifying mark;

C. determining the position of the implant (1; 15, 15') with respect to the bone (6; 16) using the radiation image received in step B;

D. repeating steps A, B, and C over time to determine migration of the implant with respect to said at least one bone;

wherein said at least one bone marking comprises an anatomically fixed point (7, 8; 13; 14) on the bone (6; 16) and said determining said position of the implant with respect to said bone is made by establishing the position of said at least one anatomically fixed point with respect to said at least one predetermined identifying mark of said implant.

2. Method according to claim 1, wherein step A comprises the following steps

A1. generating first radiation at a first position and directing the first radiation onto the at least one bone marking (7, 8; 13, 14) and the at least one predetermined identifying mark (4, 5) of the implant (1; 15, 15') from a first direction;

A2. generating second radiation at a second position and directing the second radiation onto the at least one bone marking (7, 8; 13, 14) and the at least one predetermined identifying mark (4, 5) of the implant (1; 15, 15') from a second direction; and step B comprises the following step:

B1. receiving first and second radiation images, respectively, of said at least one bone marking and said at least one predetermined identifying mark, formed by said first and second radiation, respectively; and step C comprises the following step:

C1. determining the position of the implant (1; 15, 15') with respect to the bone (6; 16) using said first and second radiation images received in step B1.

3. Method according to claim 1, wherein at least two predetermined identifying marks (4, 5) are used.

4. Method according to claim 1, wherein at least two anatomically fixed points (7, 8; 13, 14) on the bone (6; 16) are used.

5. Method according to claim 1, wherein the implant is a hip prosthesis (1), the radiation used is X-radiation and the predetermined identifying marks of the implant are objects (4, 5) which are impermeable to X-radiation.

6. Method according to claim 5, wherein the at least one bone marking is selected from the following two anatomically fixed points: trochanter major and trochanter minor.

7. Method according to claim 1, wherein the implant is a knee prosthesis (15, 15'), the radiation used is X-radiation and the predetermined identifying marks of the implant are objects (4, 5) which are impermeable to X-radiation.

8. Method according to claim 7, wherein the at least one bone marking is selected from the following two anatomically fixed points: medial epicondyle and lateral epicondyle.

9. Device for measuring a position of an implant (1; 15, 15') relative to at least one bone (6; 16) in a body, to which bone the implant is connected, which bone (6; 16) has at least one bone marking (7, 8; 13, 14), and which implant has at least one predetermined identifying mark (4, 5), provided with the following means:

A. generator means (10, 11) for generating radiation and directing said radiation onto said at least one bone marking and said at least one predetermined identifying mark;

B. receiving means (17, 18) for receiving a radiation image of said at least one bone marking and said at least one predetermined identifying mark;

C. evaluation means (12), which are coupled to the receiving means (17, 18), for determining the position of the implant (1; 15, 15') with respect to the bone (6; 16) using the radiation image received in step B;

D. means for repeating steps A, B, and C over time to determine migration of the implant with respect to said at least one bone;

wherein the evaluation means are provided with means for recognizing the shape of the at least one bone (6; 16), and for locating the at least one bone marking using an anatomically fixed point (7, 8; 13, 14) on the bone (6; 16) and said evaluation means are arranged for establishing the position of said at least one anatomically fixed point with respect to said at least one predetermined identifying mark of said implant.

10. Device according to claim 9, wherein said generator means comprise:

A1. first generating means (10) for generating first radiation at a first position and directing the first radiation onto the at least one bone marking (7, 8; 13, 14) and the at least one predetermined identifying mark (4, 5) of the implant (1; 15, 15') from a first direction;

A2. second generating means (11) for generating second radiation at a second position and directing the second radiation onto the at least one bone marking (7, 8; 13, 14) and the at least one predetermined identifying mark (4, 5) of the implant (1; 15, 15') from a second direction; and said receiving means (17, 18) are arranged for:

B1. receiving first and second radiation images, respectively, of said at least one bone marking and said at least one predetermined identifying mark, formed by said first and second radiation, respectively; and said evaluation means (12) are arranged for:

C1. determining the position of the implant (1; 15, 15') with respect to the bone (6; 16) using said first and second radiation images received by said receiving means.

11. Device according to claim 9, wherein said evaluation means are arranged for determining said position using said radiation image comprising at least two predetermined identifying marks (4, 5) on the implant.

12. Device according to claim 9, wherein said evaluation means are arranged for determining said position using said radiation image comprising at least two anatomically fixed points (7, 8; 13, 14) on the bone (6; 16).

13. Device according to claim 9, wherein the implant is a hip prosthesis (1), the generator means are X-radiation generator means and the predetermined identifying marks of the implant are objects (4, 5) which are impermeable to X-radiation.

14. Device according to claim 13, wherein the evaluation means (12) are arranged to recognize either the trochanter major or trochanter minor, or both, as the at least one bone marking.

15. Device according to claim 9, wherein the implant is a knee prosthesis (15, 15'), the generator means are X-radiation generator means and the predetermined identifying marks of the implant are objects (4, 5) which are impermeable to X-radiation.

16. Device according to claim 15, wherein the evaluation means (12) are arranged to recognize either the medial epicondyle or lateral epicondyle, or both, as the at least one bone marking.

* * * * *